United States Patent
Fan et al.

(10) Patent No.: US 8,787,519 B2
(45) Date of Patent: Jul. 22, 2014

(54) SYSTEM AND METHOD OF OPTIMIZING A REPRESENTATION OF DUAL ENERGY SPECTRAL CT IMAGES

(75) Inventors: Jiahua Fan, New Berlin, WI (US); Naveen Chandra, Waukesha, WI (US); Bruno Kristiaan Bernard De Man, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 437 days.

(21) Appl. No.: 13/174,825

(22) Filed: Jul. 1, 2011

(65) Prior Publication Data

US 2012/0039440 A1 Feb. 16, 2012

Related U.S. Application Data

(60) Provisional application No. 61/373,103, filed on Aug. 12, 2010.

(51) Int. Cl.
*A61B 6/03* (2006.01)
*A61B 6/00* (2006.01)

(52) U.S. Cl.
CPC ....................................... *A61B 6/482* (2013.01)
USPC ............................................... 378/5; 382/131

(58) Field of Classification Search
CPC ........ A61B 6/03; A61B 6/482; A61B 5/4869; A61B 6/5258; G06T 2211/408; G01N 23/046
USPC ............................. 378/5; 382/131, 5; 131/131
See application file for complete search history.

(56) References Cited

PUBLICATIONS

Wu et al., Monochromatic CT Image Representation via Fast Switching Dual kVp, Feb. 9, 2009, SPIE, vol. 7258, pp. 45-1 to 45-8.*
Zou et al., Analysis of Fast kV-switching in Dual Energy CT using a Pre-reconstruction Decomposition Technique, 2008, SPIE, vol. 6913, pp. 13-1 to 13-12.*
Kalender et al., "An Algorithm for Noise Suppression in Dual Energy CT Material Density Images," IEEE Transactions on Medical Imaging, vol. 7, No. 3, Sep. 1988, pp. 218-224.

\* cited by examiner

*Primary Examiner* — Toan Ton
*Assistant Examiner* — John Corbett
(74) *Attorney, Agent, or Firm* — Ziolkowski Patent Solutions Group, SC (57) ABSTRACT

An imaging system includes an x-ray source, a detector, a data acquisition system (DAS) operably connected to the detector, and a computer operably connected to the DAS. The computer is programmed to obtain CT scan data with two or more incident energy spectra, decompose the obtained CT scan data into projection CT data of a first basis material and a second basis material, generate a first basis material image and a second basis material image using the decomposed projection CT data, generate a first monochromatic image from the first basis material image and the second basis material image at a first energy that is selected based on an amount of correlated noise at the first energy, noise-reduce the first monochromatic image to generate a noise-reduced first monochromatic image, and generate a final monochromatic image based at least on the noise-reduced first monochromatic image.

20 Claims, 9 Drawing Sheets

SYSTEM AND METHOD OF OPTIMIZING A REPRESENTATION OF DUAL ENERGY SPECTRAL CT IMAGES

CROSS-REFERENCE TO RELATED APPLICATION

The present application is a nonprovisional of, and claims priority to, U.S. Provisional Application No. 61/373,103 filed Aug. 12, 2010, the disclosure of which is incorporated herein.

BACKGROUND OF THE INVENTION

Embodiments of the present invention relate generally to diagnostic imaging and, more particularly, to a system and method of dual energy spectral imaging having minimized noise.

Medical imaging devices comprise x-ray systems, magnetic resonance (MR) systems, ultrasound systems, computed tomography (CT) systems, positron emission tomography (PET) systems, nuclear medicine, and other types of imaging systems. Typically, in CT imaging systems, an x-ray source emits a fan or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis, which ultimately produces an image.

Generally, the x-ray source and the detector array are rotated about the gantry opening within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. Such typical systems, however, do not include an ability to discriminate spectral energy content of x-rays as they pass through an object being imaged.

However, as known in the art, dual or multi-energy spectral CT systems have been developed that can reveal the densities of different materials in an object and generate images acquired at multiple monochromatic x-ray energy levels. In the absence of object scatter, a system derives the behavior at a different energy based on a signal from two regions of photon energy in the spectrum: the low-energy and the high-energy portions of the incident x-ray spectrum. In a given energy region of medical CT, two physical processes dominate the x-ray attenuation: (1) Compton scatter and the (2) photoelectric effect. The detected signals from two energy regions provide sufficient information to resolve the energy dependence of the material being imaged. Detected signals from the two energy regions provide sufficient information to determine the relative composition of an object composed of two hypothetical materials.

Different approaches have been developed to realize dual energy or spectral imaging. To name a few, dual x-ray source and detector, single x-ray source and detector with multiple acquisitions at different kVp or interleaved with fast kVp switching capability, and single x-ray source with an energy discriminative detector, are leading techniques.

In a dual x-ray source and detector system, typically two x-ray sources are provided, each having a respective detector positioned opposite thereto such that x-rays may be emitted from each source having a different spectral energy content. Thus, based on the known energy difference of the sources, a scintillating or energy integrating device may suffice to distinguish energy content and different materials within the object being imaged.

In a single x-ray source and detector arrangement, a conventional third generation CT system may acquire projections sequentially at different peak kilovoltage (kVp) levels, which changes the peak and spectrum of energy of the incident photons comprising the emitted x-ray beams. Two scans are acquired—either (1) back-to-back sequentially in time where the scans require two rotations around the subject, or (2) interleaved as a function of the rotation angle requiring one rotation around the subject, in which the tube operates at, for instance, 80 kVp and 140 kVp potentials.

In a single x-ray source with an energy discriminative detector, energy sensitive detectors may be used such that each x-ray photon reaching the detector is recorded with its photon energy. Such systems may use a direct conversion detector material in lieu of a scintillator.

Once dual or multi-energy data is obtained, a basis material decomposition (BMD) algorithm may be applied in order to image two distinct materials, such as water and iodine, as examples. A conventional BMD algorithm is based on the concept that, in an energy region for medical CT, the x-ray attenuation of any given material can be represented by a proper density mix of two materials with distinct x-ray attenuation properties, referred to as the basis materials. The BMD algorithm computes two material density images that represent the equivalent density of one of the basis materials based on the measured projections at high and low x-ray photon energy spectra, respectively. The material density images may be further converted to form monochromatic images at other desired monochromatic energies.

However, noise in the material density images and monochromatic images is propagated during the decomposition process, and the noise is typically correlated. In other words, noise generated in both low and high kVp acquisitions typically correlates during material decomposition (MD) and propagates in subsequent generation of basis material images. Known noise reduction schemes are available, however, such schemes are typically limited to reducing negative correlated noise.

Therefore, it would be desirable to have a system and method that presents diagnostic imaging data having minimized noise in computed monochromatic images and material density images.

BRIEF DESCRIPTION OF THE INVENTION

According to an aspect of the present invention, an imaging system includes an x-ray source that emits a beam of x-rays toward an object to be imaged, a detector that receives the x-rays attenuated by the object, a data acquisition system (DAS) operably connected to the detector, and a computer operably connected to the DAS. The computer is programmed to obtain CT scan data with two or more incident energy spectra, decompose the obtained CT scan data into projection CT data of a first basis material and a second basis material, generate a first basis material image and a second basis material image using the decomposed projection CT data, generate a first monochromatic image from the first basis material image and the second basis material image at a first energy that is selected based on an amount of correlated noise at the first energy, noise-reduce the first monochromatic image to generate a noise-reduced first monochromatic image, and generate a final monochromatic image based at least on the noise-reduced first monochromatic image.

According to another aspect of the present invention, a method of imaging includes obtaining a low kVp dataset and a high kVp dataset, decomposing the low kVp dataset and the high kVp dataset into a first basis material image and a second basis material image, generating a first monochromatic image from the first basis material image and the second basis material image at a first energy that is selected based on an amount of correlated noise, noise-reducing the first monochromatic image to generate a noise-reduced first monochromatic image, and generating a final image based on the noise-reduced first monochromatic image.

According to yet another aspect of the present invention, a computer-readable storage medium having stored thereon a computer program which, when executed by a computer, will cause the computer to obtain low kVp and high kVp projection datasets, decompose the low kVp and the high kVp projection datasets into a first basis material image and a second basis material image, generate a first monochromatic image from the first basis material image and the second basis material image at a keV that is selected based on an amount of correlated noise, minimize noise in the first monochromatic image to generate a noise-minimized first monochromatic image, and generate a final image based on the noise-minimized first monochromatic image.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION

Diagnostics devices comprise x-ray systems, magnetic resonance (MR) systems, ultrasound systems, computed tomography (CT) systems, positron emission tomography (PET) systems, nuclear medicine, and other types of imaging systems. Applications of x-ray sources comprise imaging, medical, security, and industrial inspection applications. It will be appreciated by those skilled in the art that an implementation is applicable for use with single-slice or other multi-slice configurations. Moreover, an implementation is employable for the detection and conversion of x-rays. However, one skilled in the art will further appreciate that an implementation is employable for the detection and conversion of other high frequency electromagnetic energy. An implementation is employable with a "third generation" CT scanner and/or other CT systems.

The operating environment of the present invention is described with respect to a sixty-four-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
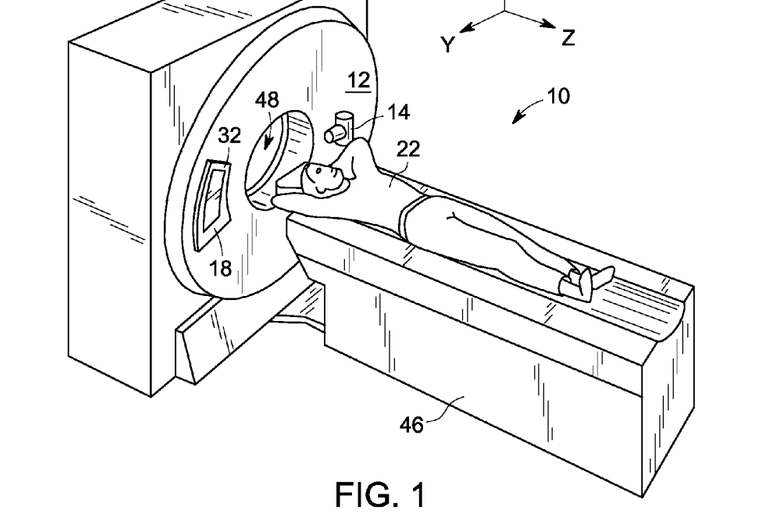
FIG. 1 is a pictorial view of a CT imaging system.
Figure 2:
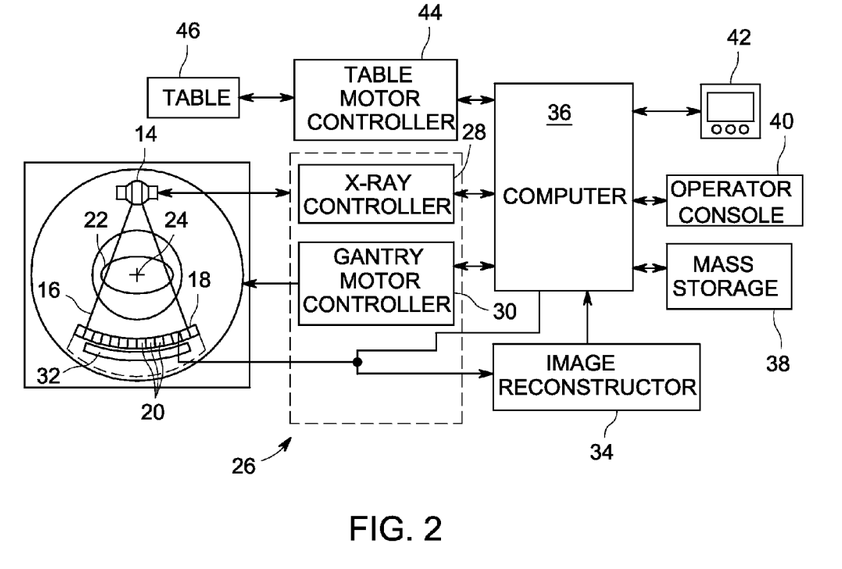
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. Detector assembly 18 is formed by a plurality of detectors 20 and data acquisition systems (DAS) 32. The plurality of detectors 20 sense the projected x-rays that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
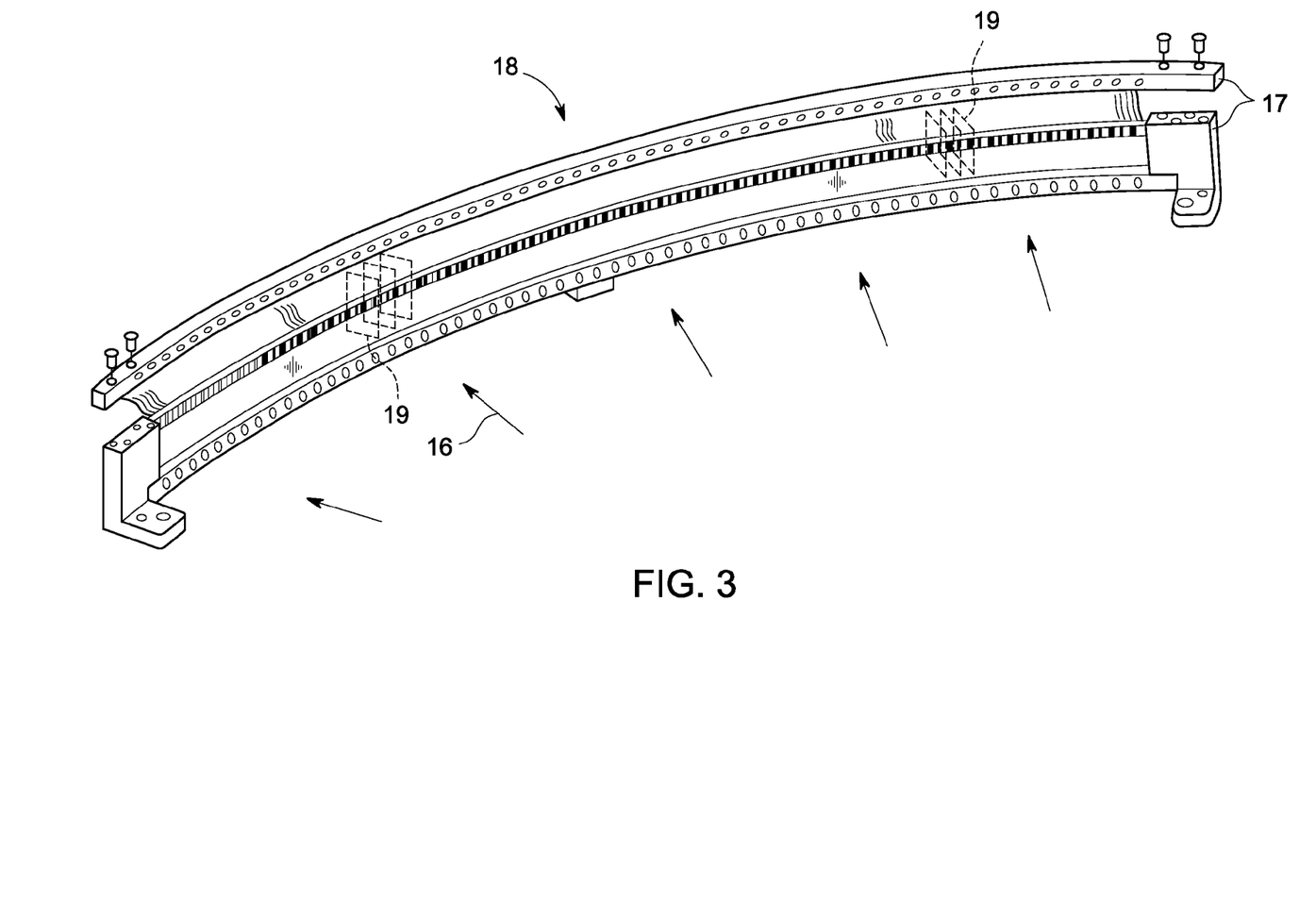
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figure 4:
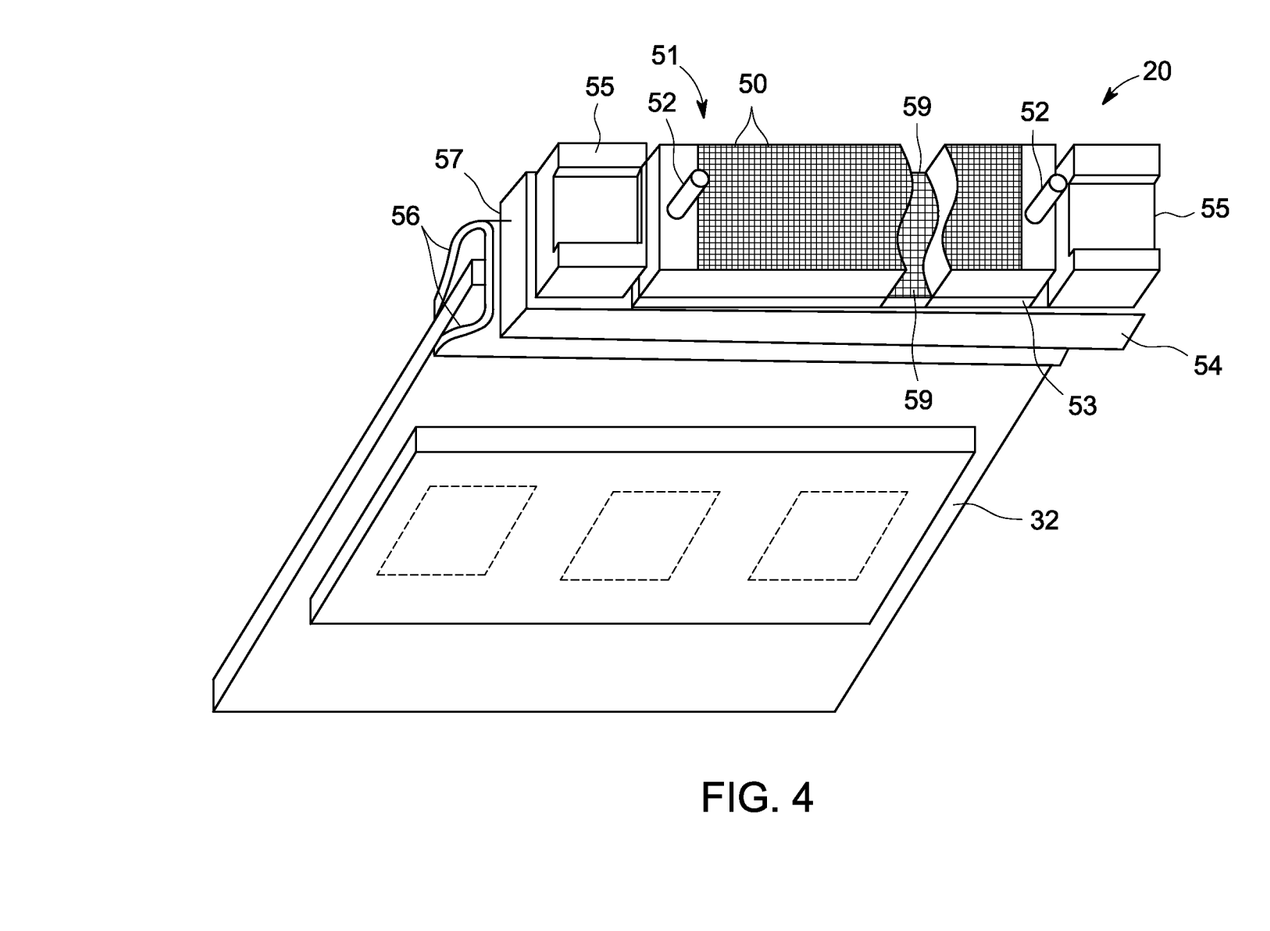
FIG. 4 is a perspective view of one embodiment of a CT detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

As described above, each detector 20 may be designed to directly convert radiographic energy to electrical signals containing energy discriminatory or photon count data. Thus, in an alternate preferred embodiment, each detector 20 includes a semiconductor layer fabricated from CZT. Each detector 20 also includes a plurality of metallized anodes attached to the semiconductor layer. Such detectors 20 may include an electrical circuit having multiple comparators thereon which may reduce statistical error due to pileup of multiple energy events.

Referring back to FIGS. 1 and 2, a discussion is now presented in connection with a decomposition algorithm. An image or slice is computed which may incorporate, in certain modes, less or more than 360 degrees of projection data to formulate an image. The image may be collimated to desired dimensions using tungsten blades in front of the x-ray source and different detector apertures. A collimator typically defines the size and shape of the beam of x-rays 16 that emerges from the x-ray source 14, and a bowtie filter may be included in the system 10 to further control the dose to the patient 22. A typical bowtie filter attenuates the beam of x-rays 16 to accommodate the body part being imaged, such as head or torso, such that, in general, less attenuation is provided for x-rays passing through or near an isocenter of the patient 22. The bowtie filter shapes the x-ray intensity during imaging in accordance with the region-of-interest (ROI), field of view (FOV), and/or target region of the patient 22 being imaged.

As the x-ray source 14 and the detector array 18 rotate, the detector array 18 collects data of the attenuated x-ray beams. The data collected by the detector array 18 undergoes pre-processing and calibration to condition the data to represent the line integrals of the attenuation coefficients of the scanned object or the patient 22. The processed data are commonly called projections.

In dual or multi-energy imaging, two or more sets of projection data are typically obtained for the imaged object at different tube peak kilovoltage (kVp) levels, which change the peak and spectrum of energy of the incident photons comprising the emitted x-ray beams or, alternatively, at a single tube peak kilovoltage (kVp) level or spectrum with an energy resolving detector of the detector array 18. The acquired sets of projection data may be used for basis material decomposition (BMD). During BMD, the measured projections are converted to a set of density line-integral projections. The density line-integral projections may be reconstructed to form a density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the CT system 10 reveals internal features of the patient 22, expressed in the densities of the two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In addition to a CT number or Hounsfield value, an energy selective CT system can provide additional information related to a material's atomic number and density. This information may be particularly useful for a number of medical clinical applications, where the CT number of different materials may be similar but the atomic number may be quite different. For example, calcified plaque and iodine-contrast enhanced blood may be located together in coronary arteries or other vessels. As will be appreciated by those skilled in the art, calcified plaque and iodine-contrast enhanced blood are known to have distinctly different atomic numbers, but at certain densities these two materials are indistinguishable by CT number alone.

A decomposition algorithm is employable to generate atomic number and density information from energy sensitive x-ray measurements. Multiple energy techniques comprise dual energy, photon counting energy discrimination, dual layered scintillation and/or one or more other techniques designed to measure x-ray attenuation in two or more distinct energy ranges. As an example, a compound or mixture of materials measured with a multiple energy technique may be represented as a hypothetical material having the same x-ray energy attenuation characteristics. This hypothetical material can be assigned an effective atomic number Z. Unlike the atomic number of an element, effective atomic number of a compound is defined by the x-ray attenuation characteristics, and it needs not be an integer. This effective Z representation property stems from a well-known fact that x-ray attenuation in the energy range useful for diagnostic x-ray imaging is strongly related to the electron density of compounds, which is also related to the atomic number of materials.

The basis for the disclosed approach for minimizing noise in basis material images is to separate noise content into orthogonal (or pseudo-orthogonal) portion and apply noise reduction separately. In such fashion negative correlated noise and non-negative correlated noise can be captured and treated independently from one another.

Denoting $P_h$ and $P_l$ as the projection measurements from respective high and low spectrum imaging, $\sigma_h$ and $\sigma_l$ are the corresponding standard deviations associated therewith. Because $P_h$ and $P_l$ are independent measurements, the noise of $P_h$ and $P_l$ are also independent. Thus, one embodiment for noise reduction is to suppress the noise of $P_h$ and $P_l$ independently, and then use noise-reduced $P_h$ and $P_l$ to derive MD and monochromatic images. One skilled in the art will recognize that the noise reduction schemes described in the literature can still be applied to further reduce noise in the MD and monochromatic images.

Figure 5:
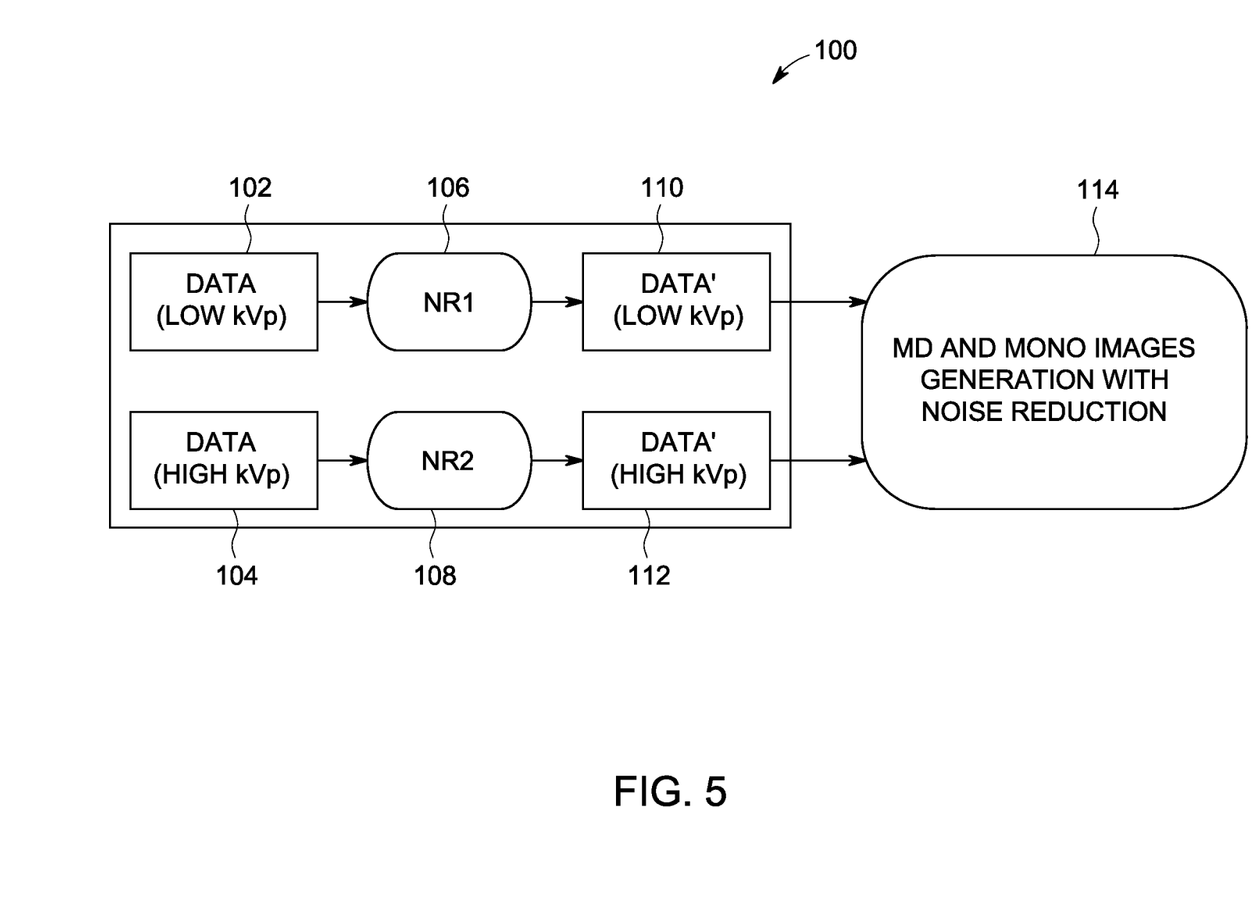
FIG. 5 is an illustration of a technique that separates noise content in projection space according to an embodiment of the invention.

Referring now to FIG. 5, a technique 100 is illustrated that separates noise content in projection space and prior to material decomposition and generation of monochromatic images from a dual energy process. Technique 100 illustrates acquisition of low kVp data 102 and acquisition of high kVp data 104. Each dataset 102, 104 may be respectively noise-reduced 106, 108 (NR1, NR2) to generate noise-reduced low kVp data 110 and noise-reduced high kVp data 112. Subsequently, as understood in the art, MD and monochromatic image generation may proceed at step 114. As such, an amount of correlated noise in subsequent steps is reduced, as noise-correlation typically occurs during the decomposition process.

Two basis MD images M1(r) and M2(r) can be expressed as:

$$M1(r)=S1(r)+NCN1(r)+NNCN1(r), \quad \text{EQN. 1,}$$

$$M2(r)=S2(r)+NCN2(r)+NNCN2(r), \quad \text{EQN. 2,}$$

where r refers to the pixel location, S1 and S2 are respective material density values of the two basis materials, NCN1 and NCN2 are the negative correlated noise content in M1 and M2, and NNCN1 and NNCN2 are the non-negative correlated noise content in M1 and M2. For simplicity, r will be omitted in subsequent discussions.

As known in the art, typically noise reduction refers to an optimal reduction of negative correlated noise contents in M1 and M2. Because monochromatic images can be generated by a weighted linear combination of two MDs and using weighting constants c1(keV1) and c2(keV2), at a certain energy level keV1, the NCN1 and NCN2 are cancelled out. That is, Mono(keV1)=$c1$(keV1)*M1+$c2$(keV1)*M2, which equals $c1$(keV1)*(S1+NCN1+NNCN1)+$c2$(keV1)*(S2+NCN2+NNCN2), which equals $c1$(keV1)*(S1+NNCN1)+$c2$(keV1)*(S2+NNCN2).

$$\text{Thus, } c1(\text{keV1})*NCN1+c2(\text{keV1})*NCN2=0, \quad \text{EQN. 3.}$$

As such, noise in a monochromatic image at energy level keV1 is primarily non-negative correlated noise.

Figure 6:
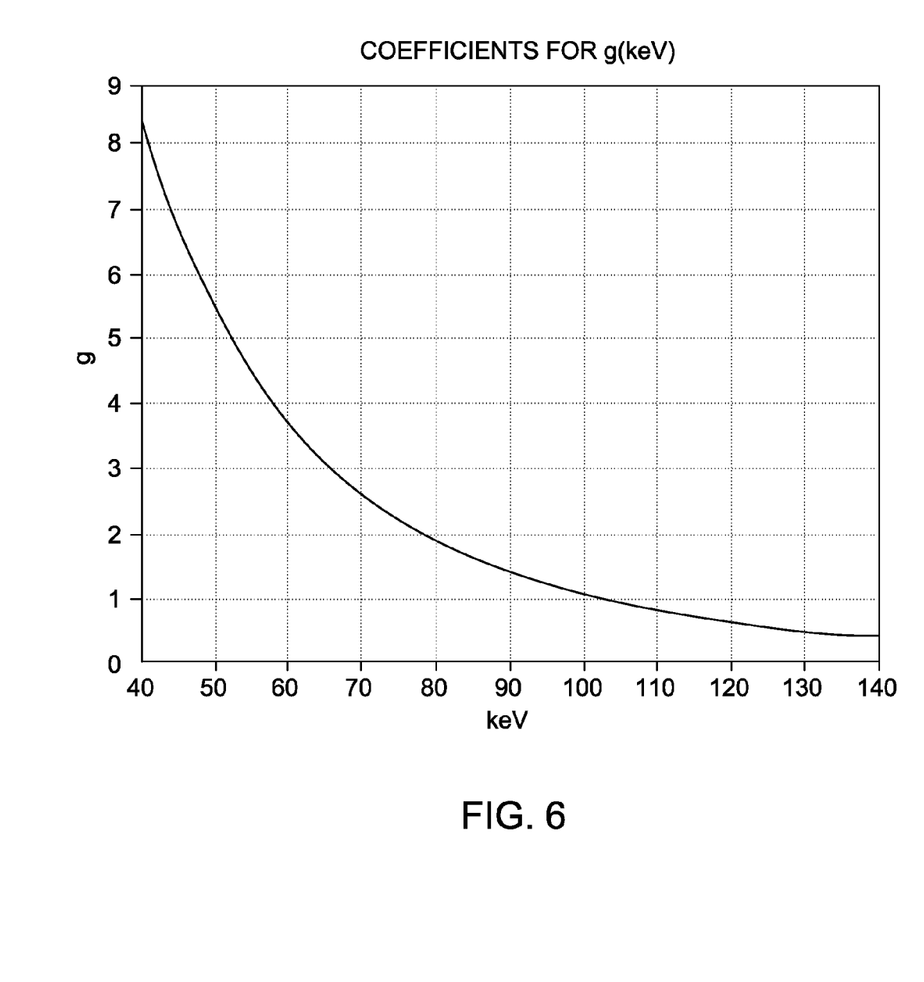
FIG. 6 is a curve that illustrates a g(keV)=c2(keV)/c1(keV) curve for M1=water, and M2=iodine.

FIG. 6 illustrates, as an example, a g(keV)=$c2$(keV)/$c1$(keV) curve for M1=water, and M2=iodine. Note that when keV increases, c1 takes on a more dominant affect. And, it has been demonstrated that in two MD and in certain monochromatic images, the dominant noise is the negative-correlated noise. Thus, a monochromatic image may be chosen at keV2, whose noise is dominated by the negative-correlated noise. As such, noise content is separated between Mono(keV1) and Mono(keV2).

Accordingly, noise reduction can be done individually on Mono(keV1) and Mono(keV2). From the two noise-reduced monochromatic images, new MD images can be generated using the inverse of the monochromatic generation function. And finally, new noise-reduced monochromatic images at all the energy levels can be generated.

Figure 7:
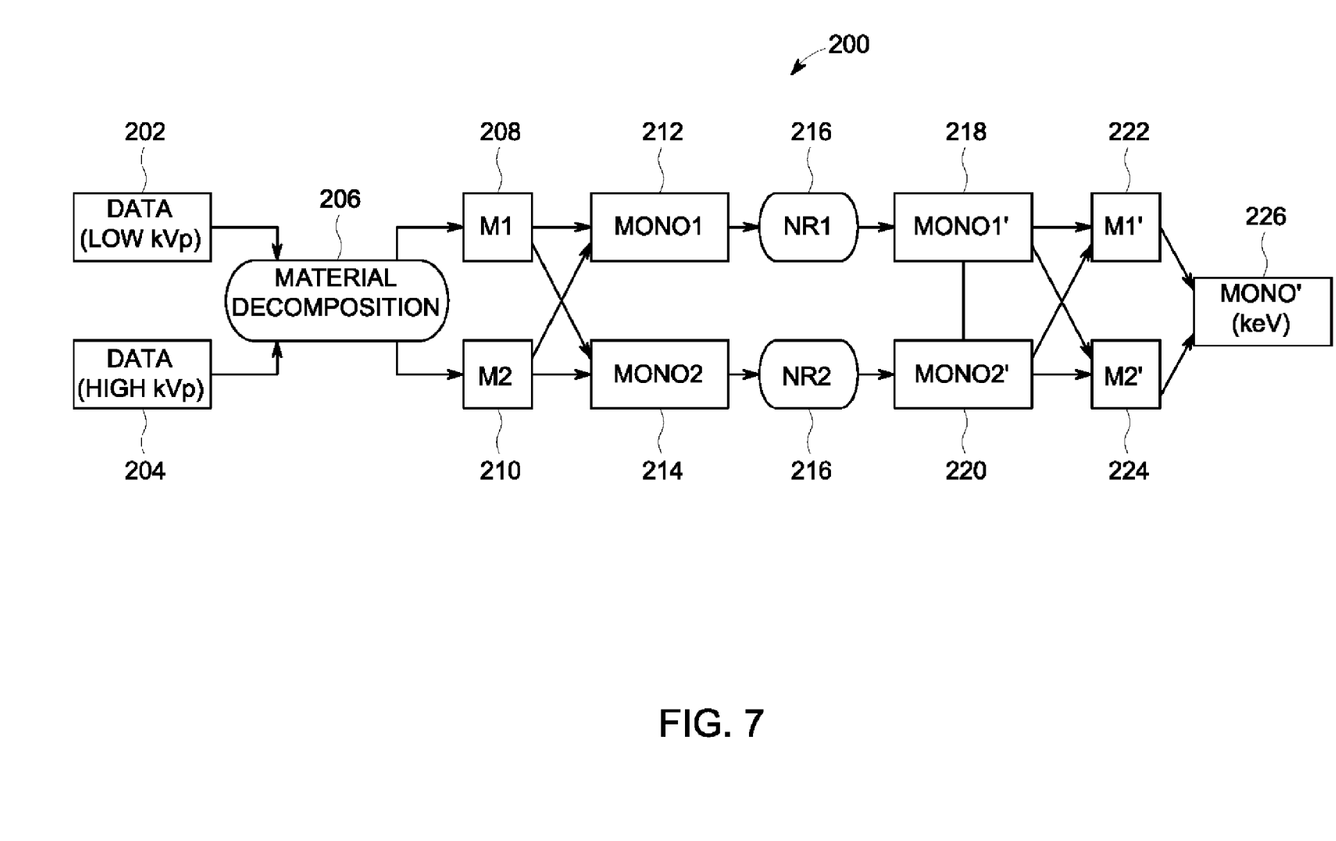
FIG. 7 is an illustration of a technique that separates noise content in projection space after material decomposition according to an embodiment of the invention.

Thus, referring to FIG. 7, a technique 200 is shown that illustrates material decomposition according to an embodiment of the invention. Technique 200 includes acquisition of low kVp data 202 and high kVp data 204. Material decomposition (MD) 206 occurs, as understood in the art, from which a first material image 208 (M1) and a second material image 210 (M2) are generated. In one embodiment, first material image 208 is water, and second material image 210 is iodine. However, embodiments of the invention are not so limited, and it is to be understood that any material combination may be considered.

According to embodiments of the invention, a first monochromatic image 212 (MONO1) is generated from first material image 208 and second material image 210, and a second monochromatic image 214 (MONO2) is generated from first material image 208 and second material image 210. First and second monochromatic images 212, 214 are generated at respective keVs that are selected based on an amount of correlated noise therein. More specifically, selection of each respective keV for first and second monochromatic images 212, 214 is based on minimizing respective amounts of negatively correlated noise and non-negatively correlated noise. Selection of keV for first and second monochromatic images 212, 214 is illustrated in reference to FIG. 8.

Figure 8:
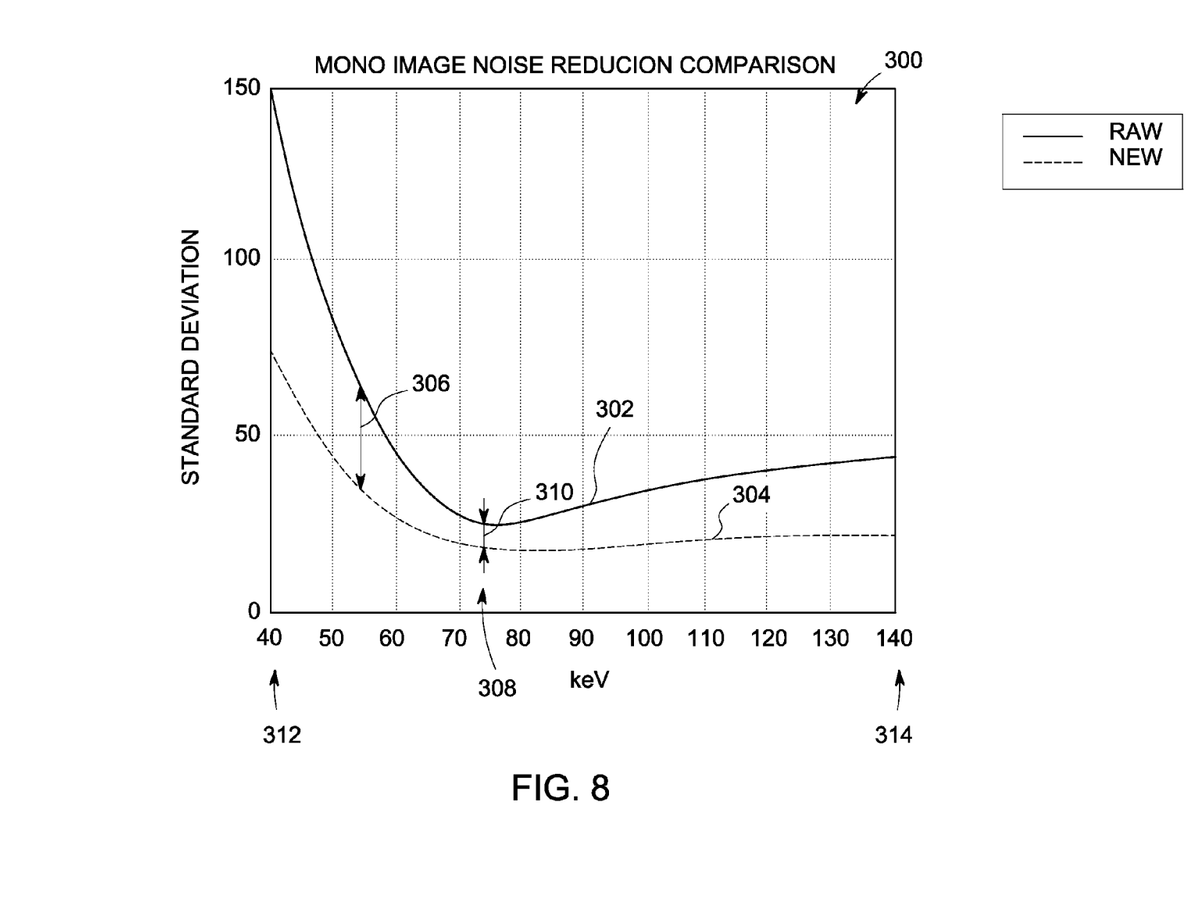
FIG. 8 is a comparison of noise in terms of a standard deviation before and after noise reduction.

FIG. 8 provides an example of a comparison 300 of noise in terms of a standard deviation before noise reduction 302 and after noise reduction 304 for monochromatic images ranging from 40 keV to 140 keV. A vertical distance 306 between both curves 302, 304 is a function of both negatively correlated noise and non-negatively correlated noise. Negatively correlated noise is at a minimum at a location 308. Thus, referring to FIGS. 7 and 8, first monochromatic image 212 may be reconstructed from first material image 208 and second material image 210 at a keV that corresponds to location 308 where negatively correlated noise is at a minimum. Location 308, wherein negatively correlated noise is a minimum, may be selected in different fashions, according to embodiments of the invention.

In one embodiment, location 308 is selected as simply a default value. For instance, in a water/iodine basis material combination, minimization occurs at approximately 73 keV. For other basis material combinations, a default minimal location may be determined based on the other basis material combinations. In another embodiment, location 308 may be selected based on a priori information such as scanning protocol, anatomy, and the like. In yet another embodiment, location 308 may be selected based on a scout image. And in still another embodiment, location 308 may be numerically determined in real-time or "on the fly" based on first material image 208 and second material image 210, as examples.

Thus, noise in monochromatic image at location 308 having difference 310 is largely attributable to non-negatively correlated noise. Correspondingly, at extremes of the keV spectrum under consideration (40 keV and 140 keV, in this example), non-negatively correlated noise is minimized with respect to negatively correlated noise, which is itself dominant or at a maximum. Accordingly, second monochromatic image 214 may be reconstructed from first material image 208 and second material image 210 at a keV that corresponds to extremes of the keV spectrum, such as at 40 keV 312 or at 140 keV 314. In another embodiment, the second monochromatic image may be generated using a calculated keV setting, which is out of the 40~140 keV range. And, it is to be recognized that embodiments of the invention disclosed herein are not to be limited to the examples of 40 keV and 140 keV, but that any keV may be selected based on an amount of correlated noise.

As such, monochromatic images 212, 214 are generated from first material image 208 and second material image 210 at corresponding keVs that are selected such that their noise contributions are orthogonal to one another. As such, each image 212, 214 may be noise-reduced 216 (NR1, NR2) to generate corresponding noise-reduced first monochromatic image 218 (MONO1') and noise-reduced second monochromatic image 220 (MONO2'). The noise-reduced first monochromatic image 218 and noise-reduced second monochromatic image 220 may then be used to generate noise-reduced first material image 222 (M1') and noise-reduced second material image 224 (M2') which, as stated above, may correspond respectively to water and iodine. As is known in the art, once noise-reduced material images 222, 224 are generated, a noise-reduced monochromatic image 226 (MONO'(keV)) may be generated at a select keV from noise-reduced material images 222, 224.

Thus, according to this embodiment, monochromatic images 212, 214 may be generated at keVs that are selected based on an amount of correlated noise therein. By appropriately selecting the keVs as discussed, a large noise standard deviation reduction for the two MD images is also achieved. Further noise reduction may be achieved beyond the optimal negative noise reduction, as understood in the art.

That illustrated with respect to FIG. 7 is applicable to both projection domain and image domain, and reconstruction steps can be inserted at any place in this flow chart, according to embodiments of the invention. Typically, it is preferred to perform the decomposition in the projection domain, followed by steps 208-226 as discussed.

Figure 9:
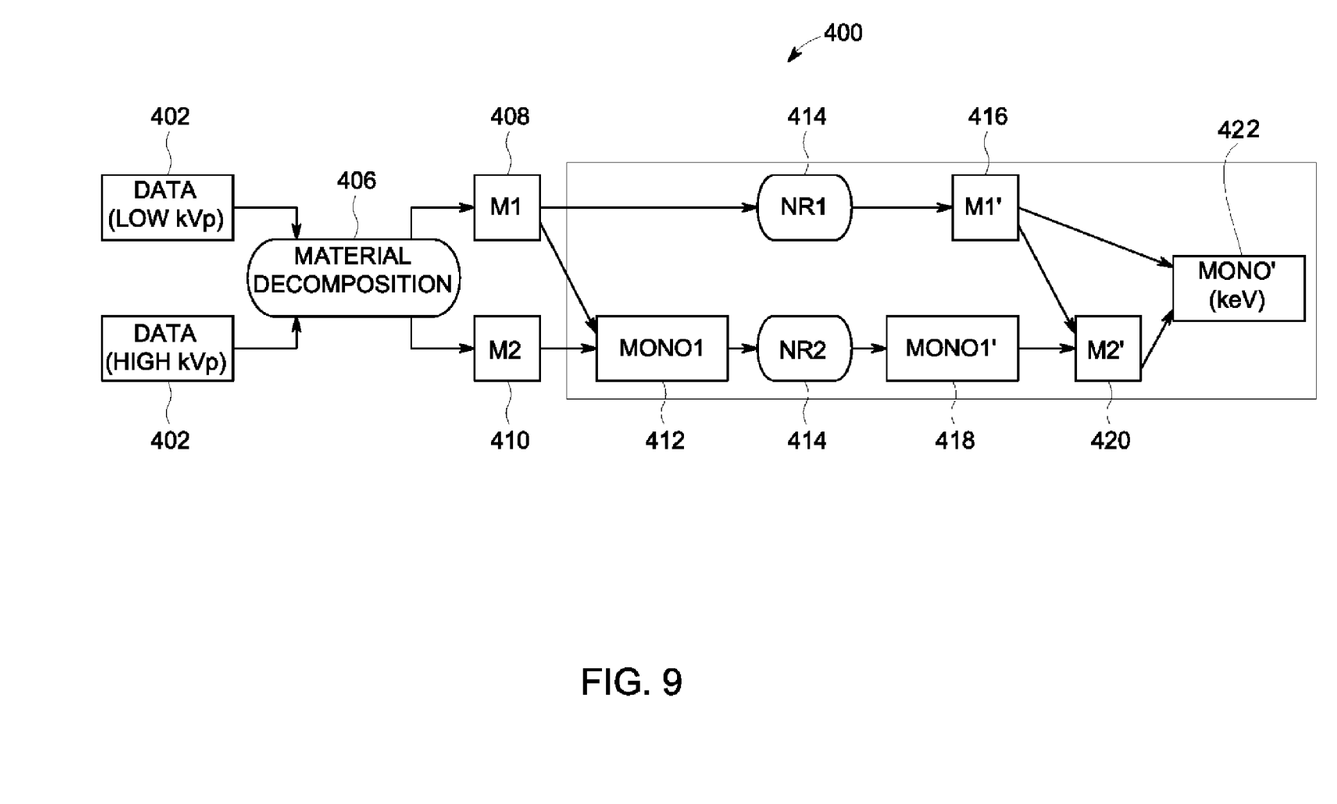
FIG. 9 is an illustration of a technique that separates noise content in projection space after material decomposition according to an embodiment of the invention.

Noise content may be separated according to another embodiment of the invention. Referring to FIG. 9, technique 400 includes acquisition of low kVp data 402 and high kVp data 404. Material decomposition (MD) 406 occurs, as understood in the art, from which a first material image 408 (M1) and a second material image 410 (M2) are generated. Steps 402-410, thus far, are similar to corresponding steps 202-210, of technique 200. However, in this embodiment, a first monochromatic image 412 (MONO1) is generated from first material image 408 and second material image 410. Noise reduction steps 414 (NR1, NR2) occur, resulting in a noise-reduced first material image 416 (M1'), and a noise-reduced monochromatic first image 418 (MONO1'), as illustrated. Noise-reduced first material image 416 and noise-reduced monochromatic first image 418 may be used to generate a noise-reduced second material image 420 (M2'), and noise-reduced first material image 416 and noise-reduced second material image 420 may be used to generate a noise-reduced monochromatic image 422 (MONO' (keV)) at a select keV.

Figure 10:
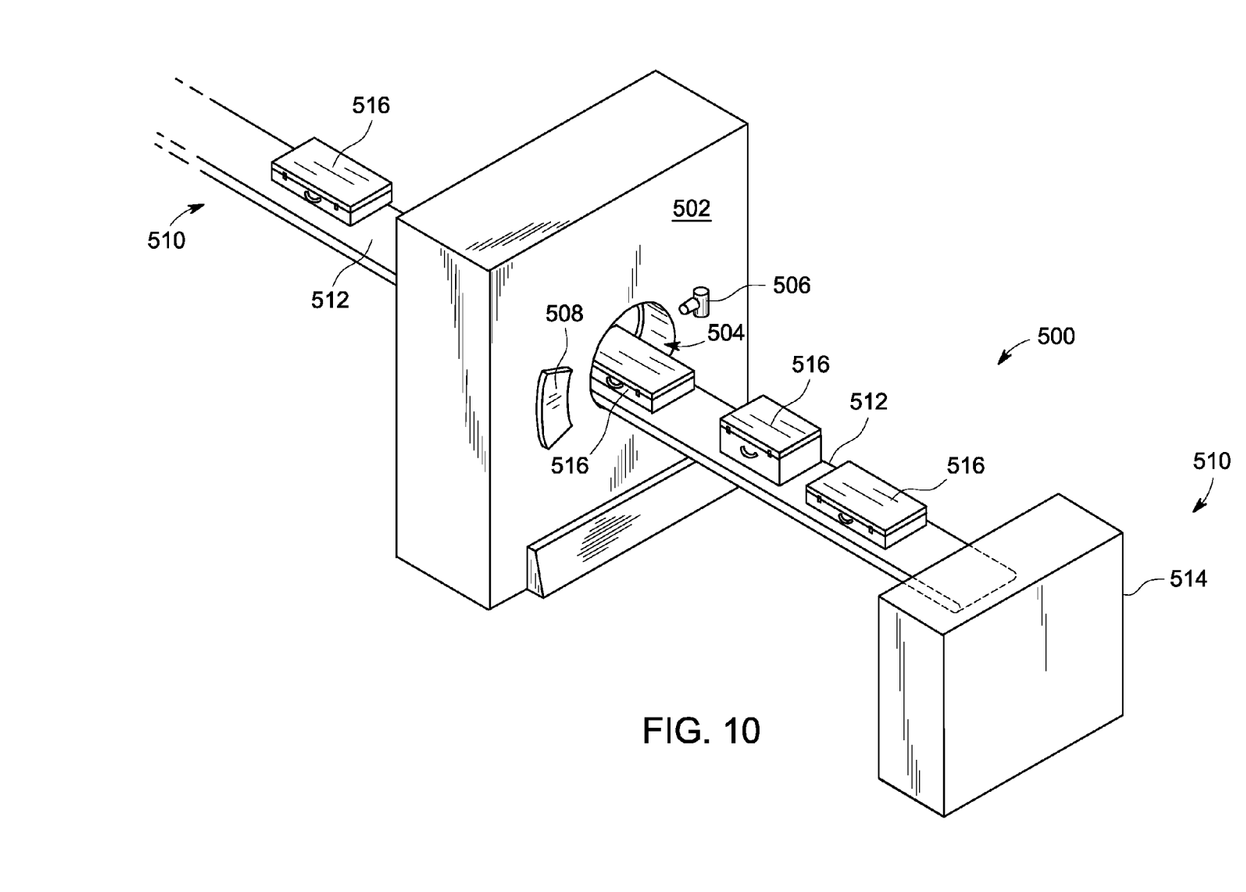
FIG. 10 is a pictorial view of a CT system for use with a non-invasive package inspection system.

Referring now to FIG. 10, package/baggage inspection system 500 includes a rotatable gantry 502 having an opening 504 therein through which packages or pieces of baggage may pass. The rotatable gantry 502 houses an x-ray and/or high frequency electromagnetic energy source 506 as well as a detector assembly 508 having scintillator arrays comprised of scintillator cells. A conveyor system 510 is also provided and includes a conveyor belt 512 supported by structure 514 to automatically and continuously pass packages or baggage pieces 516 through opening 504 to be scanned. Objects 516 are fed through opening 504 by conveyor belt 512, imaging data is then acquired, and the conveyor belt 512 removes the packages 516 from opening 504 in a controlled and continuous manner. As a result, postal inspectors, baggage handlers, and other security personnel may non-invasively inspect the contents of packages 516 for explosives, knives, guns, contraband, etc. An exemplary implementation can aid in the development of automatic inspection techniques, such as explosive detection in luggage.

An implementation of embodiments of the invention in an example comprises a plurality of components such as one or more of electronic components, hardware components, and/or computer software components. A number of such components can be combined or divided in an implementation of the embodiments of the invention. An exemplary component of an implementation of the embodiments of the invention employs and/or comprises a set and/or series of computer instructions written in or implemented with any of a number of programming languages, as will be appreciated by those skilled in the art.

An implementation of the embodiments of the invention in an example employs one or more computer readable storage media. An example of a computer-readable signal-bearing medium for an implementation of the embodiments of the invention comprises the recordable data storage medium of the image reconstructor 34, and/or the mass storage device 38 of the computer 36. A computer-readable storage medium for an implementation of the embodiments of the invention in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory.

Therefore, according to an embodiment of the invention, an imaging system includes an x-ray source that emits a beam of x-rays toward an object to be imaged, a detector that receives the x-rays attenuated by the object, a data acquisition system (DAS) operably connected to the detector, and a computer operably connected to the DAS. The computer is programmed to obtain CT scan data with two or more incident energy spectra, decompose the obtained CT scan data into projection CT data of a first basis material and a second basis material, generate a first basis material image and a second basis material image using the decomposed projection CT data, generate a first monochromatic image from the first basis material image and the second basis material image at a first energy that is selected based on an amount of correlated noise at the first energy, noise-reduce the first monochromatic image to generate a noise-reduced first monochromatic image, and generate a final monochromatic image based at least on the noise-reduced first monochromatic image.

According to another embodiment of the invention, a method of imaging includes obtaining a low kVp dataset and a high kVp dataset, decomposing the low kVp dataset and the high kVp dataset into a first basis material image and a second basis material image, generating a first monochromatic image from the first basis material image and the second basis material image at a first energy that is selected based on an amount of correlated noise, noise-reducing the first monochromatic image to generate a noise-reduced first monochromatic image, and generating a final image based on the noise-reduced first monochromatic image.

According to yet another embodiment of the invention, a computer-readable storage medium having stored thereon a computer program which, when executed by a computer, will cause the computer to obtain low kVp and high kVp projection datasets, decompose the low kVp and the high kVp projection datasets into a first basis material image and a second basis material image, generate a first monochromatic image from the first basis material image and the second basis material image at a keV that is selected based on an amount of correlated noise, minimize noise in the first monochromatic image to generate a noise-minimized first monochromatic image, and generate a final image based on the noise-minimized first monochromatic image.

The invention has been described in terms of the preferred embodiment, and it is recognized that equivalents, alternatives, and modifications, aside from those expressly stated, are possible and within the scope of the appending claims.

What is claimed is:

1. An imaging system comprising:
   an x-ray source that emits a beam of x-rays toward an object to be imaged;
   a detector that receives the x-rays attenuated by the object;
   a data acquisition system (DAS) operably connected to the detector; and
   a computer operably connected to the DAS and programmed to:
      obtain CT scan data with two or more incident energy spectra;
      decompose the obtained CT scan data into projection CT data of a first basis material and a second basis material;
      generate a first basis material image and a second basis material image using the decomposed projection CT data;
      generate a first monochromatic image from the first basis material image and the second basis material image at a first energy that is selected based on an amount of correlated noise at the first energy;
      noise-reduce the first monochromatic image to generate a noise-reduced first monochromatic image; and
      generate a final monochromatic image based at least on the noise-reduced first monochromatic image; and
   wherein the computer is further programmed to:
      noise-reduce the first basis material image to generate a noise-reduced first basis material image;
      generate a noise-reduced second basis material image using the noise-reduced first monochromatic image and the noise-reduced first basis material image; and
      generate the final monochromatic image using the noise-reduced second basis material image.

2. The imaging system of claim 1 wherein the first basis material image is one of an iodine image and a water image.

3. The imaging system of claim 1 wherein the computer is programmed to generate the first monochromatic image at the first energy, wherein the first energy is selected based on an amount of negatively correlated noise at the first energy.

4. The imaging system of claim 3 wherein the amount of negatively correlated noise is minimized at the first energy.

5. The imaging system of claim 1 wherein the computer is programmed to:
   generate a second monochromatic image from the first basis material image and the second basis material image at a second energy that is selected based on an amount of correlated noise at the second energy;
   noise-reduce the second monochromatic image to generate a noise-reduced second monochromatic image; and
   generate the final monochromatic image based on the noise-reduced second monochromatic image.

6. The imaging system of claim 5 wherein the computer is programmed to generate the second monochromatic image at the second energy that is selected based on an amount of negatively correlated noise at the second energy.

7. The imaging system of claim 6 wherein the amount of negatively correlated noise is dominant at the second energy.

8. The imaging system of claim 5 wherein the computer is programmed to:
   generate a noise-reduced first basis material image from the noise-reduced first monochromatic image and the noise-reduced second monochromatic image;
   generate a noise-reduced second basis material image from the noise-reduced first monochromatic image and the noise-reduced second monochromatic image; and
   generate the final image using the noise-reduced first basis material image and the noise-reduced second basis material image.

9. A method of imaging comprising:
   obtaining a low kVp dataset and a high kVp dataset;
   decomposing the low kVp dataset and the high kVp dataset into a first basis material image and a second basis material image;
   generating a first monochromatic image from the first basis material image and the second basis material image at a first energy that is selected based on an amount of correlated noise;
   generating a second monochromatic image from the first basis material image and the second basis material image at a second energy that is selected based on an amount of correlated noise;
   noise-reducing the first monochromatic image to generate a noise-reduced first monochromatic image;
   noise reducing the second monochromatic image to generate a noise-reduced second monochromatic image; and
   generating a final image based on the noise-reduced first monochromatic image and the noise-reduced second monochromatic image.

10. The method of claim 9 wherein the first basis material is one of water and iodine.

11. The method of claim 9 wherein generating the first monochromatic image is at the first energy that is based on an amount of negatively correlated noise.

12. The method of claim 11 wherein the amount of negatively correlated noise is minimized.

13. The method of claim 9 comprising:
   generating a noise-reduced first basis material image using the noise-reduced first monochromatic image and the noise-reduced second monochromatic image;
   generating a noise-reduced second basis material image using the noise-reduced first monochromatic image and the noise-reduced second monochromatic image; and
   generating the final image using the noise-reduced first basis material image and the noise-reduced second basis material image.

14. The method of claim 9 comprising noise-reducing the first basis material image to generate a noise-reduced first basis material image.

15. The method of claim 14 comprising generating a noise-reduced second basis material image using the noise-reduced first monochromatic image and the noise-reduced first basis material image.

16. A non-transitory computer-readable storage medium having stored thereon a computer program which, when executed by a computer, will cause the computer to:
   obtain low kVp and high kVp projection datasets;
   decompose the low kVp and the high kVp projection datasets into a first basis material image and a second basis material image;
   generate a first monochromatic image from the first basis material image and the second basis material image at a keV that is selected based on an amount of correlated noise;
   minimize noise in the first monochromatic image to generate a noise-minimized first monochromatic image;
   generate a second monochromatic image from the first basis material image and the second basis material image at a keV that is selected based on an amount of correlated noise;

minimize noise in the second monochromatic image to generate a noise-minimized second monochromatic image; and generate a final image based on the noise-minimized first monochromatic image and the noise-minimized second monochromatic image.

17. The non-transitory computer-readable storage medium of claim 16 wherein the computer is programmed to generate the first monochromatic image at a keV where non-negatively correlated noise is minimized.

18. The non-transitory computer-readable storage medium of claim 16 wherein the computer is programmed to:

generate a noise-minimized first basis material image using the noise-minimized first monochromatic image and the noise-minimized second monochromatic image;

generate a noise-minimized second basis material image using the noise-minimized first monochromatic image and the noise-minimized second monochromatic image; and generate the final image using the noise-minimized first basis material image and the noise-minimized second basis material image.

19. An imaging system comprising:

an x-ray source that emits a beam of x-rays toward an object to be imaged;

a detector that receives the x-rays attenuated by the object;

a data acquisition system (DAS) operably connected to the detector; and a computer operably connected to the DAS and programmed to:

obtain CT scan data with two or more incident energy spectra;

decompose the obtained CT scan data into projection CT data of a first basis material and a second basis material;

generate a first basis material image and a second basis material image using the decomposed projection CT data;

generate a first monochromatic image from the first basis material image and the second basis material image at a first energy that is selected based on an amount of correlated noise at the first energy;

noise-reduce the first monochromatic image to generate a noise-reduced first monochromatic image; and generate a final monochromatic image based at least on the noise-reduced first monochromatic image; and wherein the computer is further programmed to:

generate a second monochromatic image from the first basis material image and the second basis material image at a second energy that is selected based on an amount of correlated noise at the second energy;

noise-reduce the second monochromatic image to generate a noise-reduced second monochromatic image; and generate the final monochromatic image based on the noise-reduced second monochromatic image.

20. A method of imaging comprising:

obtaining a low kVp dataset and a high kVp dataset;

decomposing the low kVp dataset and the high kVp dataset into a first basis material image and a second basis material image;

noise-reducing the first basis material image to generate a noise-reduced first basis material image;

generating a first monochromatic image from the first basis material image and the second basis material image at a first energy that is selected based on an amount of correlated noise;

noise-reducing the first monochromatic image to generate a noise-reduced first monochromatic image;

generating a noise-reduced second basis material image using the noise-reduced first monochromatic image and the noise-reduced first basis material image and generating a final image based on the noise-reduced first monochromatic image.

* * * * *